US008263132B2

(12) United States Patent
Blair et al.

(10) Patent No.: US 8,263,132 B2
(45) Date of Patent: Sep. 11, 2012

(54) METHODS FOR PREPARING PHARMACEUTICALS BY EMULSION AGGREGATION PROCESSES

(75) Inventors: Christopher David Blair, Webster, NY (US); Zhen Lai, Webster, NY (US); Zhaoyang Ou, Webster, NY (US); Dennis A. Mattison, Jr., Marion, NY (US); Philip J. Dale, Hamlin, NY (US); Chieh-Min Cheng, Rochester, NY (US)

(73) Assignee: Xerox Corporation, Norwalk, CT (US)

( * ) Notice: Subject to any disclaimer, the term of this patent is extended or adjusted under 35 U.S.C. 154(b) by 299 days.

(21) Appl. No.: 12/640,164

(22) Filed: Dec. 17, 2009

(65) Prior Publication Data

US 2011/0150985 A1 Jun. 23, 2011

(51) Int. Cl.
*A61K 9/14* (2006.01)
(52) U.S. Cl. ............ 424/489; 424/451; 514/772.3
(58) Field of Classification Search .................. None
See application file for complete search history.

(56) References Cited

U.S. PATENT DOCUMENTS

| | | |
|---|---|---|
| 5,278,020 A | 1/1994 | Grushkin et al. |
| 5,290,654 A | 3/1994 | Sacripante et al. |
| 5,308,734 A | 5/1994 | Sacripante et al. |
| 5,344,738 A | 9/1994 | Kmiecik-Lawrynowicz et al. |
| 5,346,797 A | 9/1994 | Kmiecik-Lawrynowicz et al. |
| 5,348,832 A | 9/1994 | Sacripante et al. |
| 5,364,729 A | 11/1994 | Kmiecik-Lawrynowicz et al. |
| 5,366,841 A | 11/1994 | Patel et al. |
| 5,370,963 A | 12/1994 | Patel et al. |
| 5,370,964 A | 12/1994 | Patel et al. |
| 5,403,693 A | 4/1995 | Patel et al. |
| 5,405,728 A | 4/1995 | Hopper et al. |
| 5,418,108 A | 5/1995 | Kmiecik-Lawrynowicz et al. |
| 5,496,676 A | 3/1996 | Croucher et al. |
| 5,501,935 A | 3/1996 | Patel et al. |
| 5,527,658 A | 6/1996 | Hopper et al. |
| 5,585,215 A | 12/1996 | Ong et al. |
| 5,593,807 A | 1/1997 | Sacripante et al. |
| 5,650,255 A | 7/1997 | Ng et al. |
| 5,650,256 A | 7/1997 | Veregin et al. |
| 5,853,944 A | 12/1998 | Foucher et al. |
| 5,919,595 A | 7/1999 | Mychajlowskij et al. |
| 5,945,245 A | 8/1999 | Mychajlowskij et al. |
| 6,294,606 B1 | 9/2001 | Chen et al. |
| 6,348,561 B1 | 2/2002 | Mychajlowskij et al. |
| 7,029,817 B2 | 4/2006 | Robinson et al. |
| 7,276,254 B2 | 10/2007 | Burns et al. |
| 7,531,334 B2 | 5/2009 | Cheng et al. |
| 2003/0211035 A1 * | 11/2003 | Burns et al. .................. 424/1.11 |
| 2006/0172956 A1 * | 8/2006 | Bonner et al. .................. 514/35 |
| 2006/0223934 A1 | 10/2006 | Chen et al. |
| 2008/0236446 A1 | 10/2008 | Zhou et al. |
| 2008/0248126 A1 * | 10/2008 | Cheng et al. .................. 424/497 |

OTHER PUBLICATIONS

Chew et al., "The Role of Particle Properties in Pharmaceutical Powder Inhalation Formulations," Journal of Aerosol Medicine, vol. 15, No. 3, pp. 325-330, Sep. 2002.

* cited by examiner

*Primary Examiner* — Johann Richter
*Assistant Examiner* — Daniel L Branson
(74) *Attorney, Agent, or Firm* — Oliff & Berridge, PLC

(57) ABSTRACT

A method for making a pharmaceutical by emulsion aggregation, the method including emulsifying a first pharmaceutical agent and a biodegradable resin to form a primary emulsion of pre-aggregated particles in a slurry; aggregating the pre-aggregated particles to form aggregated pharmaceutical particles in the slurry; and isolating the pharmaceutical particles. The method may be used to make time-released, multi-formulation, and inhalable pharmaceuticals.

18 Claims, No Drawings

METHODS FOR PREPARING PHARMACEUTICALS BY EMULSION AGGREGATION PROCESSES

TECHNICAL BACKGROUND

This disclosure is generally directed to methods of preparing pharmaceuticals and to pharmaceutical compositions formed by using such methods. More particularly, this disclosure is directed to using emulsion aggregation processes for producing timed-release, multi-formulation, and/or inhalable pharmaceuticals.

BACKGROUND

Particle size, particle composition, and particle size distribution control are important for the production and manufacture of pharmaceuticals. These factors play a role in pharmaceutical treatment regimens, including dosage amounts, dosage frequency, active-ingredient concentration, and drug therapy side effects. These factors also contribute to pharmaceutical engineering.

In particular, particle size distribution control is important for timed-release pharmaceuticals. Within the same binder system, a large particle size will give relatively long release, while smaller sizes will give relatively shorter releases. For example, a sleep aid may claim to help a user fall asleep quickly and then stay asleep. This could be accomplished by quickly delivering the active ingredient at first, and then slowly delivering the active ingredient over time.

Similarly, particle size distribution control is important for multi-formulation pharmaceuticals. For example, some pharmaceuticals contain two or more active agents to be delivered simultaneously or at spaced intervals. There exists a need in the industry of a predictable and efficient method of making multi-formulation pharmaceuticals capable of delivering in a controlled manner multiple active agents.

Particle size distribution control is also important for pharmaceuticals employed in dry powder inhaler (DPI) systems. An article by Chew et al. describes the use, importance, and challenges of DPI systems and pharmaceutical powders in medicine. See Nora Y. K. Chew et al., 15(3) Journal of Aerosol Medicine 325-330 (September 2002) (doi:10.1089/089426802760292672). Generally, the chemical stability of dry powders is greater than liquid formulations used in atomizers. However, dry powder formulation and production can be difficult because of the nature of pharmaceuticals and of micro- or nano-sized particles. For example, micro- and nano-sized particles can be adhesive and cohesive, leading to agglomeration problems in both aerosol performance and variable dosage.

Emulsion aggregation processes are known to be used for making polymeric microspheres for use in some biomedical applications. For example, U.S. Pat. Nos. 7,276,254 and 7,531,334 (both owned by Xerox), the entire disclosures of which are incorporated herein by references, describe using microspheres produced by emulsion aggregation processes to carry biomedical functional materials attached on the surface of the microsphere for various applications (e.g. in cell culture applications).

However, there exists a need to more accurately and predictably control particle size distribution, methods of producing particles for DPI systems, and methods of producing particles capable of controlled active agent(s) release.

SUMMARY

The methods described herein result in various, significant advantages over typical methods for producing pharmaceuticals. For example, controlling the particle size distribution and make-up of a pharmaceutical enables a constant release of the pharmaceutical over a given time period, provides for a more therapeutic drug, eliminates or decreases multiple administrations of the pharmaceutical, prevents oscillating levels of the pharmaceutical (high levels after the dose, followed by low levels until the next dose), provides a user with a more simple treatment regimen, and decreases side effects.

The present disclosure in embodiments addresses these various needs by providing a method for producing timed-release, multi-formulation, and/or inhalable pharmaceuticals by an emulsion aggregation process. The emulsion aggregation process represents a novel means to accurately control particle size, avoid agglomeration of particles (allowing for their use in DPI systems), and provide layers within the particles for multi-formulation and/or timed-release pharmaceuticals.

In embodiments, the method comprises: emulsifying a first pharmaceutical agent and a biodegradable resin to form a primary emulsion of pre-aggregated particles in a slurry; aggregating the pre-aggregated particles to form aggregated pharmaceutical particles in the slurry; and isolating the pharmaceutical particles. The method may be used to make time-released, multi-formulation, and inhalable pharmaceuticals.

Embodiments also include time-released, multi-formulation, and inhalable pharmaceuticals made by the methods described herein.

These and other improvements are accomplished by the methods described in embodiments herein.

EMBODIMENTS

The present invention provides a process for making timed-release, multi-formulation, and/or inhalable pharmaceuticals and for specifically controlling particle size and size distribution by using emulsion aggregation processes. In embodiments, "pharmaceutical" means a substance or combination of substances that includes a bioactive agent. Pharmaceuticals may include a polymer, a bioactive agent, and optional additives.

In this specification and the claims that follow, singular forms such as "a," "an," and "the" include plural forms unless the content clearly dictates otherwise. All ranges disclosed herein include, unless specifically indicated, all endpoints and intermediate values. In addition, the terms "optional" or "optionally" refer, for example, to instances in which subsequently described circumstance may or may not occur, and include instances in which the circumstance occurs and instances in which the circumstance does not occur. Also, the terms "one or more" and "at least one" refer, for example, to instances in which one of the subsequently described circumstances occurs, and to instances in which more than one of the subsequently described circumstances occurs.

Polymers

In embodiments for time-release, multi-formulation, and/or inhalable pharmaceuticals, at least one biodegradable polymer and/or resin is used. "Biodegradable polymer" refers to polymers or resins that can be metabolized or broken down by a biological process in an organism in such a way that a pharmaceutical that is encapsulated, dispersed, bound, etc. to the polymer is released during the course of treatment. In embodiments, biodegradable polymers include any polymers that can be aerobically or anaerobically broken down in an organism. For example, some biodegradable resins may be broken down by an organism into $CO_2$ and $H_2O$.

Examples of biodegradable polymers that may be used alone or in combination with other biodegradable polymers include poly(lactic acid), poly(glycolic acid) (PGA), poly (lactic-co-glycolic acid) (PLGA), poly(lactic acid-co-polyethylene oxide), poly(s-caprolactone), poly(propylene fumarate) (PPF), poly(butylene succinate) (PBS), polyhydroxyalkanoate (PHA), polyhydroxybutyrate (PHB), polydioxanone, polyimide esters, polyalkalene esters, and polyvinyl esters, and copolymers thereof.

Natural polymers may also be used alone or in combination with the above polymers. Illustrative examples of natural polymers include polysaccharides such as cellulose, starch, collagen, gelatin, and chitosan.

In embodiments, the resin does not denature or disassociate during the emulsion aggregation process.

The resin may be optionally functionalized to promote aggregation and/or to facilitate the attachment of a bioactive agent molecule to the resin chain being aggregated. Any functional group must be bio-compatible so as to not poison the user of the pharmaceutical to be produced. For example, in styrene polymers an acrylate such as a beta-carboxyethyl acrylate (β-CEA) may be used. Although β-CEA is toxic by ingestion as a raw material, it is not as toxic when included on a polymer chain. However, alternatives with lower toxicity are known in the art and may be used in embodiments herein. Any positively charged functional group may work, for example, carboxylate groups, chlormethyl groups, aliphatic amine groups, and aldehyde/sulfate groups.

Bioactive Agents

In embodiments, the pharmaceutical includes a bioactive agent. "Bioactive agent" means a substance or combination of substances intended for use in the diagnosis, cure, mitigation, inducement, treatment, or prevention of disease, medical conditions and symptoms, and psychological conditions and symptoms. In embodiments, the term "bioactive agent" encompasses, for example, drugs. Bioactive agents may include, for example, anti-proliferative agents, steroids, analgesics, narcotic antagonists, antibiotics, anti-fungals, anti-histamines, anti-asthmatics, beta-blockers, anti-cancer agents, amino acids, vitamins, enzymes, nutrients (such as proteins and carbohydrates), probiotic micro-organisms, prebiotic foods, mineral salts, mixes of acids (such as lactic acid, fumaric acid, citric acid, and malic acid), choline, and choline derivatives, and mixtures thereof. Other examples of bioactive agents include psychotropic medications such as neurotransmitter re-uptake inhibitors (SSRI, SNRI, etc.), anti-depressants, trycyclic anti-depressants, anti-psychotics, atypical anti-psychotics, benzodiazepines, stimulants, mood stabilizers, depressants, and mixtures thereof.

In embodiments, one or more bioactive agents may be added to the resin emulsion in an amount of from about 0.01% to about 65% by weight of the particle solids, such as from about 0.5% to about 10% by weight of particle solids. In embodiments, the bioactive agent does not denature or disassociate during the emulsion aggregation process. Also, in embodiments, the bioactive agent may be combined with or carried on any suitable carrying substance. The bioactive agents may be encapsulated by the resin particles in whole or in part. The resulting mixture may optionally be dispersed utilizing, for example, a Brinkman or IKA homogenizer.

Optional Additives

One or more optional additives may be added to the resin emulsion. For example, suitable additives include, but are not limited to, colorants, magnetic materials, superparamagnetic materials, radioactive materials, imaging contrasts, stabilizers, flocculants, and the like.

Colorants may be used, among other things, for identification and/or labeling purposes. For example, one or more colorants, such as pigments or dyes, can be added to the resin emulsion in an amount of from 0% to about 65% by weight of the particle solids, such as from about 0.5% to about 35% by weight of particle solids.

Magnetic materials may be used for imaging and for administration of treatment. For example, ferromagnetic materials are magnetic materials that heat under an alternating, appropriately oriented, magnetic field. They heat until they reach their Curie point, or the temperature at which they become non-magnetic and stop heating. Ferromagnetic materials may be used to ablate tumors by surrounding the tumor with ferromagnetic particles and then subjecting the patient to the appropriate magnetic field. The advantages are localization of the heating so that surrounding cells are not destroyed and the self limiting heating of ferromagnetic materials.

Radioactive tracers such as yttrium-89, yttrium-90, phosphorous-31, and phosphorous-32 may be used for imaging studies. Radioactive materials may also be used for various treatments, such as treatment of cancerous tumors. Imaging contrasts may also be used such as Barium Sulfate for x-ray contrast.

Stabilizers may also be added to the resin emulsion. Examples of suitable stabilizers include water-soluble alkali metal hydroxides, such as sodium hydroxide, potassium hydroxide, lithium hydroxide, beryllium hydroxide, magnesium hydroxide, calcium hydroxide, or barium hydroxide; ammonium hydroxide; alkali metal carbonates, such as sodium bicarbonate, lithium bicarbonate, potassium bicarbonate, lithium carbonate, potassium carbonate, sodium carbonate, beryllium carbonate, magnesium carbonate, calcium carbonate, barium carbonate or cesium carbonate; or mixtures thereof.

Flocculants or surfactants may be added to the resin emulsion. Examples of suitable flocculants or cationic surfactants include dialkyl benzenealkyl ammonium chloride, dialkylbenzene dialkylammonium chloride, lauryl trimethyl ammonium chloride, alkylbenzyl methyl ammonium chloride, alkyl benzyl dimethyl ammonium bromide, benzalkonium chloride, cetyl pyridinium bromide, C-12, C-15, C-17 trimethyl ammonium bromides, halide salts of quaternized polyoxyethylalkylamines, dodecylbenzyl triethyl ammonium chloride, MIRAPOL ALKAQUAT available from Alkaril Chemical Company, SANIZOL (benzalkonium chloride) available from Kao Chemicals, polyaluminum chloride (PAC), polyaluminum sulfate silicate (PASS), aluminum sulfate cationic salts (such as, for example, magnesium chloride, zinc acetate, calcium chloride, or the like), and the like, whether alone or in combination or mixture with other flocculants or cationic surfactants. Such flocculants or cationic surfactants may be included in effective amounts of, for example, from about 0.01 percent to about 10 percent by weight. In some embodiments, the molar ratio of the cationic surfactant used for flocculation to the anionic surfactant used in the polymer/resin preparation is in the range of from about 0.5 to 4. It is to be understood that other useful anionic and cationic surfactants will become readily apparent to one of skill in the art based on the present disclosure.

Other various and suitable additives known in the art of pharmaceutical production and emulsion aggregation particle preparation may be optionally added at any stage in the below described process, for example, prior to, during, or after emulsion formation; prior to, during, or after aggregation; and prior to, during, or after coalescence of the pharmaceutical particles.

Emulsion Aggregation Processes

In embodiments, the pharmaceuticals are made using emulsion aggregation processes. Emulsion aggregation processes for making particles, for example colored particles for use in electrophotographic and other imaging processes, in which the particles are achieved via aggregation as opposed to particle size reduction, are well known. Such emulsion aggregation processes generally include the steps of emulsion, aggregation, coalescence, washing, and drying. For example, emulsion aggregation processes for the preparation of toner particles are illustrated in a number of Xerox patents, the disclosures of which are totally incorporated herein by reference, such as U.S. Pat. Nos. 5,290,654, 5,278,020, 5,308,734, 5,370,963, 5,370,964, 5,344,738, 5,403,693, 5,418,108, 5,364,729, and 5,346,797. Also of interest may be U.S. Pat. Nos. 5,348,832, 5,405,728, 5,366,841, 5,496,676, 5,527,658, 5,585,215, 5,650,255, 5,650,256, 5,501,935, 6,294,606, 5,593,807, 5,604,706, 5,853,944, 5,919,595, 6,348,561, and 5,945,245, the entire disclosures of which are also incorporated herein by reference.

Emulsion Formation. If the bioactive agent and resin have solubility parameters that are similar, the same solvent may be used to dissolve the bioactive agent and the resin to produce a homogeneous solution. The resin and bioactive agent may be emulsified together, especially if they are both soluble in the same solvent, or alternatively, a resin emulsion may first be produced, followed by the addition of the bioactive agent to the resin emulsion. In embodiments, the emulsion may be emulsified mechanically or chemically.

For example, phase inversion emulsification (PIE) may be used where both the bioactive agent and the polymer are dissolved in a suitable solvent. Water may be added to the solvent until separation of the solvent and water occurs under mixing. The solvent may be removed by vacuum distillation and an emulsion of polymer and bioactive agent microshopheres in water results. For a description of PIE process see U.S. Pat. No. 7,029,817; U.S. Patent Application Pub. No. 2006/0223934; and U.S. Patent Application Publication No. 2008/0236446, the entire disclosures of which are incorporated herein by reference.

The emulsion may be prepared by dissolving a resin, such as a polyester resin, in a solvent. Suitable solvents include alcohols, ketones, esters, ethers, chlorinated solvents, nitrogen containing solvents and mixtures thereof. Specific examples of suitable solvents include isopropyl alcohol, acetone, methyl acetate, methyl ethyl ketone, tetrahydrofuran, cyclohexanone, ethyl acetate, N,N dimethylformamide, dioctyl phthalate, toluene, xylene, benzene, dimethylsulfoxide, and mixtures thereof. The resin may be dissolved in a solvent at an elevated temperature of from about 40° C. to about 80° C., such as from about 50° C. to about 70° C., or from about 60° C. to about 65° C. The resin is dissolved at a temperature below the boiling point of the solvent, such as from about 2° C. to about 15° C. or from about 5° C. to about 10° C. below the boiling point of the solvent, and at a temperature lower than the glass-transition temperature of the resin.

After being dissolved in a solvent, the dissolved resin may be mixed into an emulsion medium, for example water, such as deionized water containing an optional stabilizer and an optional surfactant.

Next, the mixture may be heated to flash off the solvent, and then cooled to room temperature. The solvent flashing may be conducted at any suitable temperature above the boiling point of the solvent in water that will flash off the solvent, such as from about 60° C. to about 100° C., from about 70° C. to about 90° C., or about 80° C., although the temperature may be adjusted. Solvent flashing is typically performed under vacuum to increase the solvent stripping rate. An optional defoamer may be added to decrease foam generation during solvent stripping Following the solvent flash step, the polyester resin emulsion may have an average particle diameter in the range of from about 100 nm to about 500 nm, such as from about 130 nm to about 300 nm as measured with a Honeywell MICROTRAC® UPA150 particle size analyzer.

In another embodiment, an emulsion is prepared by agitating in water a mixture of one or more of an optional nonionic surfactant, such as polyethylene glycol or polyoxyethylene glycol nonyl phenyl ether, an optional anionic surfactant, such as sodium dodecyl sulfonate or sodium dodecyl benzenesulfonate, a biodegradable resin, and an optional bioactive agent.

In embodiments, the resulting emulsion sized resin particles may have a volume average diameter of from about 20 nm to about 1200 nm specifically including all sub-ranges and individual values within the range of about 20 nm to about 1200 nm. The resulting resin emulsion, which typically contains from about 20% to about 60% solids, may be diluted with water to about 15% solids. A bioactive agent may be added at this point to the resin emulsion if such a component has not been previously added or if additional bioactive agents are desirable that were not included in the above formed resin emulsion processes.

In embodiments, additional optional additives, such as colorants, magnetic materials, superparamagnetic materials, radioactive materials, imaging contrasts, stabilizers, flocculants, may be added to the resin emulsion. When additives, including bioactive agents, are incorporated into the resin emulsion, optional flocculation of the emulsion may be conducted to assist in the polymeric microsphere production. When so conducted, a flocculant is added to effect flocculation of the additives with the emulsion resin particles.

Aggregation. The optionally flocculated resin-additive mixture is then suitably homogenized, for example, at from about 2000 to about 6000 rpm, to form statically bound pre-aggregated particles. The statically bound pre-aggregated particles are then heated at a suitable temperature below the glass-transition temperature of the resin to form aggregated particles. For example, the pre-aggregated particles may be heated to from about 40° C. to about 60° C., such as from about 30° C. to about 50° C. or from about 35° C. to about 45° C. The particles may be heated for a suitable duration of time of, for example, from about 30 minutes to about 600 minutes, such as from about 60 minutes to about 400 minutes, or from about 200 minutes to about 300 minutes.

At this point, the particle size and distribution is "frozen" by pH adjustment, and is optionally coalesced to form polymeric pharmaceutical particles of a controlled size with narrow size distribution.

Coalescence. After freezing the growth of the aggregated particles at the desired size, the aggregated particles may optionally again be heated to a suitable temperature at or above the glass-transition temperature of the resin(s) to coalesce the aggregated particles into coalesced particles. For example, the aggregated particles may be heated to from about 60° C. to about 100° C., such as from about 70° C. to about 90° C., or from about 75° C. to about 85° C. The particles may be heated for a suitable duration of time of, for example, about 30 minutes to about 600 minutes, such as from about 60 minutes to about 400 minutes, or from about 200 minutes to about 300 minutes.

Once the pharmaceutical particles are formed, they may be isolated from the reaction mixture by any suitable means, Suitable isolation methods include filtration, particle classification, and the like.

The formed pharmaceutical particles may optionally be washed, dried, and/or classified by any known conventional means. For example, the formed pharmaceutical particles can be washed using, for example, water, deionized water, or other suitable materials. The formed pharmaceutical particles may likewise be dried using, for example, a heated drying oven, a spray dryer, a flash dryer, pan dryer freeze dryer, or the like.

Following the optional particle classification, washing and/or drying, the polymeric particles may be subjected to an optional chemical surface treatment. For example, the polymeric particles may be subjected to any desirable surface treatment to alter the chemical and/or physical properties of the particle, such as hydrophobicity, hydrophilicity, surface charge, and the like, or to attach or alter functional groups present on the surface of the particles.

In embodiments, the pharmaceutical emulsion aggregation particles may be made to have a small size (VolD50), for example, from about 3 µm to about 10 µm, from about 5.2 µm to about 6 µm, or about 5.6 µm.

These particles may have an excellent particle size distribution, particularly compared to the scattered distribution typically exhibited from polymeric particles prepared by grinding techniques. In addition, emulsion aggregation particles can have specific surface treatments and shapes depending on the process conditions, which can be important parameters in various end-product uses.

The pharmaceutical particles may also have a size such that the upper geometric standard deviation (GSD) by volume is in the range of from about 1.15 to about 1.23, such as about 1.18; and a lower geometric standard deviation (GSD) by number in the range of from about 1.20 to about 1.30, such as about 1.20. These GSD values for the particles of the present disclosure indicate that the particles are made to have a very narrow particle size distribution. The upper GSD is calculated from the cumulative volume percent finer than measurement and is the ratio of the 84 percent finer than (D84v) by volume to the 50 percent finer than (D50v) by volume; it is often notated D84/50v. The lower GSD is calculated from the number percent finer than measurement and is the ratio of the 50 percent finer than (D50n) by number to the 16 percent finer than (D16n) by number; it is often notated as D50/16n.

The particle shape may also be controlled. The particles may have a shape factor of about 105 to about 170, such as about 110 to about 160, SF1*a. Scanning electron microscopy (SEM) is used to determine the shape factor analysis of the particles by SEM and image analysis (IA) is tested. The average particle shapes are quantified by employing the following shape factor (SF1*a) formula: $SF1*a=100\ \pi d^2/(4A)$, where A is the area of the particle and d is its major axis. A perfectly circular or spherical particle has a shape factor of exactly 100. The shape factor SF1*a increases as the shape becomes more irregular or elongated in shape with a higher surface area.

In addition to measuring shape factor, another metric to measure particle circularity uses an FPIA-2100 or FPIA 3000, manufactured by Sysmex. This method more quickly quantifies the particle shape. For a completely circular sphere the circularity would be 1.000. In embodiments, the particles can have circularity of about 0.920 to 0.990, such as from about 0.950 to about 0.985.

The pharmaceutical particles optionally may be treated with a suitable flow aid(s) and/or mixed with a large spacer molecule(s) to decrease agglomeration of the pharmaceutical particles. Such additives must be bio-compatible and appropriate for the method of administration of the pharmaceutical (ingestion, inhalation, injection, etc.). For example, poly(m-ethyl methacrylate) (PMMA) may be used as a large spacer molecule to decrease agglomeration.

After particle formation, the particles may be administered as, for example, a dry powder for a DPI system, pressed into a tablet, encapsulated (for example in a gel capsule), or the like.

Shell Formation. Alternatively, a shell or multiple shells may be added to the core aggregated particles prior to coalescence. A core-shell structure may be used to provide both time-release pharmaceuticals and multi-formulation pharmaceuticals. In forming a shell, the core is aggregated to a pre-determined size with a first mixture of components. A shell resin with the second mixture of components is then added to the reaction and aggregation proceeds to a second target particle size. This can be repeated several times to form multiple shells of varying thicknesses and components as desired. For example, from 2 to about 10 shells may be added to the core, such as from about 2 to about 5, or from about 3 to about 4. If desired, more than 10 shells may be provided.

The shell or shells may comprise varying concentrations of a single bioactive agent, various bioactive agents, or any combination of bioactive agent in various concentrations. The shell or shells may also be added in varying thicknesses according to the desired targeted pharmaceutical. For example, the shell may have a thickness of from about 0.1 µm to about 4 µm, such as from about 0.2 µm to about 2 µm, or about 0.5 µm. For instance, a thick shell with a low concentration of bioactive agent may be added to provide a slow release of the bioactive agent. Similarly, a thin shell with a high concentration of bioactive agent may be added to the core to provide an initial burst of a particular bioactive agent, followed by the administration of the core bioactive agent.

In a time-release pharmaceutical, various pharmaceutical release schedules or timelines may be designed with respect to the core and shell(s). For example, a core-shell structure may be implemented for a fast release followed by sustained slow release. In such a case, the shell would contain a higher concentration of bioactive agent relative to the core. Alternatively, a core-shell structure may be used to provide a slow release followed by a fast release. In such a case, the shell would contain a lower concentration of active ingredient relative to the core. Also, a core-shell structure may be used to provide for a constant, consistent release of an active ingredient. For example, a multi-shell structure could be configured so that as the surface area of a particle decreases during biodegradation, the concentration of the active ingredient from the shells to the core increases to provide a constant flow of active ingredient.

In a multi-formulation pharmaceutical, the core-shell structure may also be used. For example, a shell including a different active ingredient than that which is in the core may be applied after the aggregation period, before coalescence, to make a multi-formulation pharmaceutical. Thus, a single administration of the resulting multi-formulation pharmaceutical includes a first pharmaceutical that may be administered to a patient, followed by a second, different pharmaceutical.

In embodiments, the shell may also contribute to diminishing agglomeration of the pharmaceutical particles after formation. The shell latex may be designed to exclude materials prone to agglomeration, for example, pigments. Thus, even if the core contains materials prone to agglomeration, such materials may be sequestered within a shell. Thus a core-shell structure may diminish agglomeration and provide particles that are ideal for use in, for example, a DPI system.

Thus, the final particles resulting faun the emulsion aggregation process may be controlled to be finely dispersed without agglomeration, allowing for dry powder inhalers (DPI). Inhalable particulates are favored because they have a longer shelf life than liquid type inhalers.

EXAMPLES

The following Examples further exemplify preparation of pharmaceuticals by emulsion aggregation processes. These Examples are illustrative of different compositions, methods, and conditions that can be utilized in practicing the disclosure. It will be apparent, however, that the disclosure can be practiced with many types of compositions and may have many different uses in accordance with the disclosure above and as pointed out below Examples 1-5 describe various processes for forming emulsions.

Example 1

Double Emulsion-Solvent Evaporation Method (w1/o/w2)

A bioactive agent-containing aqueous phase is first poured into an organic solution of a biodegradable polymer dissolved in an organic solvent, such as ethyl acetate and methylene chloride. A primary (w1/o) emulsion is obtained by sonication of the aqueous phase and organic solution. Then, a 2% aqueous PVAL solution is poured into the primary emulsion and sonicated to form the w1/o/w2 double emulsion. The final suspension of nanoparticles is then magnetically stirred overnight at room temperature to evaporate the organic solvents.

Example 2

Solid-in Oil-in Water Method (s/o/w)

Bioactive agent molecules are directly suspended in an organic solvent, such as ethyl acetate or methylene chloride. A primary emulsion is obtained by sonication of the drug/solvent mixture to obtain a finely dispersed solid-in oil suspension (s/o). Then, a 2% aqueous PVAL solution is poured into the primary emulsion and sonicated to form the s/o/w double emulsion. The final suspension of nanoparticles is then magnetically stirred overnight at room temperature to evaporate the organic solvents.

Example 3

Phase Inversion Emulsification

A resin dispersion plus bioactive agent molecules is prepared via PIE using the following formulation: 10/5.0/1.25/84%/30 (Resin/methyl ethyl ketone (MEK)/isopropyl alcohol (IPA), ammonia/deionized water. The reactor is heated with a jacket set point of 60° C. Once the reactor reaches a temperature of 58° C., vacuum distillation begins. After 36 minutes, the reactor reaches a pressure of 74 mm of Hg. The resin dispersion is then quickly distilled, which reduces the temperature of the reactor to about 45° C. The total amount of time to reach the desired amount of residual solvents (<100 ppm) is about 14-16 hours.

Example 4

Solvent-free Emulsification

A ZSK-53 extruder, equipped with a feed hopper and liquid injection ports is heated to approximately 95° C. and fed a mixture of sodium hydroxide, DOWFAX 2A1, and a crystalline polyester resin (poly(dodecandioicacid-co-nonanediol). Water heated to 80° C. containing a bioactive agent molecule is fed into the extruder's first injection port at a feed rate of 1.0 kg/min using a diaphragm pump. The resultant extrusion yields a solvent-free emulsion.

Example 5

Emulsion Polymerization

A monomer emulsion is prepared by agitating a monomer mixture at about 300 rpm at a temperature from about 20° C. to about 25° C. in a glass 2 L reaction vessel with double P-4 impellers. The monomer mixture includes about 630 g styrene, about 140 g n-butyl acrylate, about 23.2 g beta-carboxyethyl acrylate (β-CEA), about 5.4 g 1-dodecanethiol with an aqueous solution (about 15.3 g DOWFAX 2A1 (an alkyldiphenyloxide disulfonate surfactant from Dow Chemical)), a bioactive agent molecule, and about 368 g deionized water). About 1.1 g of DOWFAX 2A1 (47% aq.) and about 736 g of deionized water are added, and deaerated for about 30 minutes while the temperature is raised to about 75° C. About 11.9 g of a monomer emulsion described above is then added into a stainless steel reactor and stirred for about 8 minutes at about 75° C. An initiator solution prepared from about 11.6 g of ammonium persulfate in about 57 g of deionized water is added to the reactor over about 20 minutes. Stirring is continued for about an additional 20 minutes to allow seed particle formation. The first half of the remaining monomer emulsion is fed into the reactor over about 130 minutes. The second half of the remaining monomer emulsion is combined with about 6.5 g of 1-dodecanethiol, and stirred at about 300 rpm for about 10 minutes. This second monomer emulsion is then fed into the reactor over about 90 minutes. At the conclusion of the monomer feed, the emulsion is post-heated to about 75° C. for about 3 hours and then cooled to a temperature of about 35° C.

Examples 6-9 describe the preparation of pharmaceutical particles.

Example 6

Preparation of Pharmaceutical Particles

A first bioactive agent/resin emulsion from one of Examples 1-5 is aggregated by heating the emulsion to from about 40° C. to about 50° C. for about 30 to about 180 minutes. The particle size is monitored via sampling with a Beckman-Coulter Counter II. When the targeted core particle size is reached, a second latex prepared according to Examples 1-5 containing the same or different concentration of bioactive agent by resin weight basis is added to the reactor and heated to about 40° C. to about 50° C. to form a shell. When a second targeted particle size is reached, the particle size growth is halted via pH adjustment. The aggregated core/shell particle is heated to about 80° C. to 90° C. and held at that temperature for from about 2 to about 4 hours until a targeted circularity is achieved as measured via a Sysmex FPIA 3000. The batch is then rapidly cooled to less than 40° C.

Example 7

Preparation of a Multi-formulation Pharmaceutical

The process of Example 6 is repeated, except that at least two different bioactive agents are incorporated into the pharmaceutical particles. A first bioactive agent is incorporated into the core and a second bioactive agent is incorporated into the shell.

Example 8

Preparation of Pharmaceutical Particles

In a 2 L reactor, 31.7 parts latex or combination of latex comprising a biodegradable polymer, 5.7 parts bioactive agent, 6.7 parts PY74 yellow pigment (solids content 19 weight percent), 0.3 parts DOWFAX surfactant, and 47 parts deionized water are combined. The pH of the mixture is adjusted to about 3.2 using a 0.3 M solution of nitric acid ($HNO_3$). Next, 1.0 parts of a 10 weight percent aluminum sulfate ($Al_2(SO_4)_3$) solution is added to the mixture which is then homogenized using a Cavitron rotor/stator homogenizer at 6000 rpm over a period of 5 minutes. The reactor is then stirred to about 300 rpm and heated to about 48° C. to aggregate the bioactive agent/resin particles.

When the size of the particles is determined to be about 5.0 μm, a shell is coated on the particles. The shell mixture comprises 15.2 parts latex or combination of latex comprising a biodegradable polymer, 0.1 parts of DOWFAX surfactant, 5.7% bioactive agent, and 100 parts of deionized water. After heating the reactor to 50° C., the size of the particles grows to 5.8 μm and the pH of the solution is adjusted to 5.0 using a 4% sodium hydroxide solution. The reactor rpm is then decreased to about 250 rpm, followed by the addition of 0.7 parts of ethylenediaminetetraacetic acid (EDTA) VERSENE 100. After adjusting and holding constant the pH of the particle solution to 7.5, the particle solution is heated to a coalescence temperature of 85° C. Once the particle solution reaches the coalescence temperature, the pH is lowered to a value of 7.3 to allow coalescence (spherodization) of the particle. After about 1.5 to 3.0 hours, the particles have the desired circularity of about 0.964 and are quenched to a temperature of less than 45° C. using a heat exchanger. Upon cooling, the particles are washed to remove any residual surfactants and/or any residual ions, and dried to a moisture content below 1.2 weight percent.

Example 9

Preparation of an Inhalable Pharmaceutical

The pharmaceutical nanoparticles obtained from any of Examples 6-8 are optionally treated with PMMA to further inhibit agglomeration. Next, the particles are incorporated into a DPI system.

It will be appreciated that various of the above-disclosed and other features and functions, or alternatives thereof, may be desirably combined into many other different systems or applications. Also, various presently unforeseen or unanticipated alternatives, modifications, variations or improvements therein may be subsequently made by those skilled in the art, and are also intended to be encompassed by the following claims.

What is claimed is:

1. A method for making a pharmaceutical by emulsion aggregation, the method comprising:

forming a primary emulsion comprising a first biodegradable polymer and a first bioactive agent;

aggregating the primary emulsion to form core particles;

forming a secondary emulsion comprising a second biodegradable polymer and a second bioactive agent;

aggregating the secondary emulsion to form particles comprising a shell;

colalescing the particles to form pharmaceutical particles; and isolating the pharmaceutical particles, wherein the first and second biodegradable polymers are preexisting polymers that were polymerized in the absence of bioactive agents.

2. The method of claim 1, further comprising washing and drying the pharmaceutical particles.

3. The method of claim 1, wherein forming the primary emulsion comprises homogenizing the first bioactive agent, the first biodegradable polymer,and an optional flocculant.

4. The method of claim 1, wherein forming the primary emulsion comprises adding a first bioactive agent to an emulsion comprising the first biodegradable polymer.

5. The method of claim 1, wherein aggregating comprises heating to a temperature below a glass-transition temperature of the respective first or second biodegradable polymer.

6. The method of claim 1, further comprising freezing by pH adjustment the particle size and distribution of the particles after aggregation.

7. The method of claim 1, wherein coalescing comprises heating to a temperature at or above the glass-transition temperature of the first and second biodegradable polymers.

8. The method of claim1, wherein the second bioactive agent is the same as the first bioactive agent.

9. The method of claim 1, wherein the concentration of the first bioactive agent in the primary emulsion is different from the concentration of the second bioactive agent in the secondary emulsion.

10. The method of claim 1, wherein the second bioactive agent is different from the first bioactive agent.

11. The method of claim 1, further comprising adding at least two shells to the particles prior to coalescence.

12. The method of claim 1, wherein the pharmaceutical particles have an average diameter of from about 3 μm to about 10 μm.

13. The method of claim 1, wherein the pharmaceutical particles have an upper geometric standard deviation by volume of from about 1.15 to about 1.23.

14. The method of claim 1, further comprising encapsulating the pharmaceutical particles in a gel capsule for administration of the pharmaceutical to a patient in need thereof.

15. The method of claim 1, further comprising pressing the pharmaceutical particles into a tablet for administration of the pharmaceutical to a patient in need thereof.

16. The method of claim 1, further comprising incorporating the pharmaceutical particles into a dry powder inhaler for the administration of the pharmaceutical to a patient in need thereof.

17. The method of claim 1, wherein the pharmaceutical particles have a shape factor of about 105 to about 170.

18. The method of claim 1, wherein the pharmaceutical particles have a circularity of about 0.920 to 0.990.

* * * * *